United States Patent
Satyanarayana

(10) Patent No.: US 6,267,888 B1
(45) Date of Patent: Jul. 31, 2001

(54) BIODISPERSION AS A METHOD FOR REMOVAL OF HYDROCARBON OIL FROM MARINE AQUEOUS ENVIRONMENTS

(76) Inventor: Ganti Satyanarayana, 4235 Beaumont Rd., Dover, PA (US) 17315

( * ) Notice: Subject to any disclaimer, the term of this patent is extended or adjusted under 35 U.S.C. 154(b) by 0 days.

(21) Appl. No.: 09/359,034

(22) Filed: Jul. 23, 1999

Related U.S. Application Data

(60) Provisional application No. 60/093,870, filed on Jul. 23, 1998.

(51) Int. Cl.[7] ............................. C02F 3/00; C12N 1/20; C12N 1/26
(52) U.S. Cl. ................. 210/610; 210/611; 210/922; 435/244; 435/248; 435/252.1; 435/253.3; 435/262.5
(58) Field of Search ..................... 210/610, 611, 210/620, 922; 435/244, 248, 261, 262, 262.5, 281, 252.1, 253.3

(56) References Cited

U.S. PATENT DOCUMENTS

| | | | |
|---|---|---|---|
| 3,510,403 | * | 5/1970 | Laine et al. . |
| 3,856,667 | * | 12/1974 | Azarowicz . |
| 3,871,956 | * | 3/1975 | Azarowics . |
| 3,871,957 | * | 3/1975 | Mohan et al. . |
| 3,883,397 | * | 5/1975 | Townsley . |
| 3,900,421 | * | 8/1975 | Fusey . |
| 3,941,692 | * | 3/1976 | Gutnick et al. . |
| 3,959,127 | | 5/1976 | Bartha et al. . |
| 4,146,470 | | 3/1979 | Mohan et al. . |
| 4,284,509 | | 8/1981 | Lindörfer et al. . |
| 4,401,762 | * | 8/1983 | Tellier et al. . |
| 4,512,914 | * | 4/1985 | Lepain et al. . |
| 5,194,161 | | 3/1993 | Heller et al. . |
| 5,252,215 | * | 10/1993 | McFarlane et al. . |
| 5,401,413 | | 3/1995 | Gatt et al. . |
| 5,451,325 | | 9/1995 | Herkenberg . |
| 5,494,580 | * | 2/1996 | Baskys et al. . |
| 5,496,723 | * | 3/1996 | Murzakov et al. . |
| 5,578,474 | | 11/1996 | Focht et al. . |
| 5,707,857 | * | 1/1998 | Schulz . |
| 5,725,885 | * | 3/1998 | Felix et al. . |

* cited by examiner

*Primary Examiner*—David A. Simmons
*Assistant Examiner*—Fred Prince
(74) *Attorney, Agent, or Firm*—Hunton & Williams

(57) ABSTRACT

A method for removal of free-floating oil from an aqueous environment by bio-dispersion and bio-utilization comprising the steps of:

(i) isolating species/strains of bacteria having an ability to utilize hydrocarbons as the only source of carbon;

(ii) admixing the bacteria with a fatty substance and hydrocarbon oil to form an oleophilic suspension comprising a physiologically active bacterial culture of hydrocarbonoclastic bacteria, the fatty substance comprising an oleophilic nutrient as a source of nitrogen and phosphorus for the bacteria, and (iii) applying the oleophilic suspension of the bacteria to a free floating oil in an aqueous environment to disperse and remove free-floating oil therefrom.

17 Claims, No Drawings

BIODISPERSION AS A METHOD FOR REMOVAL OF HYDROCARBON OIL FROM MARINE AQUEOUS ENVIRONMENTS

PRIORITY OF INVENTION

This application claims priority under 35 U.S.C. §119(e) from U.S. Provisional Application No. 60/093,870, filed Jul. 23, 1998.

BACKGROUND OF THE INVENTION (i) Field of the Invention

The present invention relates generally to cleanup of oil spills in a marine environment and, more particularly, to bioremediation or biological removal of floating oil through biodispersion.

(ii) Description of Related Art

Pollution of rivers, streams, harbors, bays, beaches and the open sea by hydrocarbon oil has increased tremendously in recent years. It is difficult to assess the quantity of polluting oil in any aqueous environment, since the oil generally transforms into the following four states on encountering water. These are a) as film on water, b) as solution in dissolved state, c) as emulsion of oil in water and d) in the form of tar balls. It is possible that only laser acoustic instruments may provide absolute values for the thickness of oil.

It has been reported that at least 10% of the volume of oil being transported through tankers and super tankers finds its way to estuaries and harbors polluting these environments. The volume of oil discharged through handling and transportation in addition results in a release of millions of gallons of oil into the sea. Although a major oil spill may occur in mid-ocean, actual harmful effects are felt only in the coastal regions and estuaries. The pollution of water by oil therefore, is not regarded as an oceanic problem but a coastal hazard.

Presently only two methods are generally regarded as safe in removing floating oil from any environment. One is physical removal of floating oil employing mechanical skimmer and suction devices of various types. The second one is bioremediation of contaminating oil. Although mechanical skimmers are effective in removing oil after oil spills of major or minor nature, the mechanical process does not remove all the oil completely and the residual oil once again finds its way to coastal regions or estuaries and beaches.

Bioremediation has been recognized as a technology to combat oil pollution through an environmentally friendly technique. The technology has been employed for shoreline clean up in Alaska after the accidental spill of 11 million gallons of crude oil spilled from the tanker EXXON VALDEZ in 1989. Results of massive experiments undertaken for the clean up of the shore line along the coast of Alaska by the representatives of U.S. Environmental Protection Administration (E.P.A) and those of EXXON Co. Houston have been published by both the U.S. E.P.A. and EXXON in 1991 and 1992, respectively. Thus a technology for shoreline clean up through bioremediation has been demonstrated which even today remains successful in a limited way.

Problems in harbors and ports are of a different nature and can not be subjected to the same technology. Bioremediation by addition of oil degrading microbes is often promoted as a treatment of floating spills, but this approach has not met with any documented success (Prince, 1998). Thus, the treatment for a floating oil spill requires a totally new approach.

SUMMARY AND OBJECTS OF THE INVENTION

The present overcomes the limitations described above with respect to the related art in that it removes floating oil in enclosed masses through a process identified as "biodispersion" which is followed by "bioutilization."

The method of the present invention meets all of the requirements necessary for an oil spill cleanup technique, which is harmless to marine life of economic importance or otherwise. In addition the method has the advantage of preventing the extensive loss of bird life. The method explores the possibilities of pretreatment of ballast water and bilge water before its release by tankers and ships. The method can also be used for treatment of refinery effluents and for industrial waste water remediation.

In a first aspect, the present invention relates to a method for removal of free-floating oil from an aqueous environment by bio-dispersion and bio-utilization comprising the steps of:

(i) isolating a consortium or a strain of bacteria having an ability to utilize hydrocarbons as the only source of carbon;

(ii) admixing the bacteria with a hydrocarbon source to form an oleophilic suspension comprising a physiologically active bacterial culture of hydrocarbonoclastic species; and (iii) applying the oleophilic suspension of the bacteria to a free floating oil in an aqueous environment to disperse and remove free-floating oil therefrom.

The bacterium is preferably obtained from the aqueous environment to be treated. In general, the suspension will comprise a multiple species or strains of bacteria. The species or strains of bacteria are advantageously derived from Pseudomonas, Phenylobacterium, Stenotrophomonas, Gluconobacter, Agrobacterium, Vibrio, Acinetobacter, or Micrococcus. yeasts or other genera can also be employed. Exemplary bacterial strains include *Pseudomonas pseudoalkaligenes, Phenylobacterium immobile, Stenotrophomonas maltophilia, Gluconobacter cerinus, Agrobacterium radiobacter* or *Pseudomonas alcaligenes*.

It is also within the scope of the present invention to employ bacteria which have been genetically manipulated.

Suitable fatty substances for admixture with the bacteria in forming the oleophilic suspension include oleic acid, ricinic acid and other organic fatty acids available synthetically or through natural sources. Advantageously, the fatty substance is mixed with an oil such as diesel oil. The fatty substance can further comprise a oleophilic nutrients such as nitrogen and phosphorus in a state of micro-emulsion, a particularly preferred oleophilic nutrient being INIPOL®.

In addition to oil spills, the aqueous environment treated can further include, by way of example, ballast water, bilge water or refinery wastewater. Furthermore, the water can be saline or freshwater.

In a second aspect, the present invention relates to an oleophilic suspension comprising a fatty substance and a physiologically active bacterial culture of hydrocarbonoclastic bacteria for removing free floating oil from an aqueous environment by bio-dispersion followed by bio-utilization.

In a preferred embodiment, the physiologically active bacterial culture of hydrocarbonoclastic bacteria are indigenous to the aqueous environment. Exemplary bacteria are derived from Pseudomonas, Phenylobacterium, Stenotrophomonas, Gluconobacter, Agrobacterium, Vibrio, Acinetobacter, or Micrococcus. Exemplary species include

*Pseudomonas pseudoalkaligenes, Phenylobacterium immobile, Stenotrophomonas maltophilia, Gluconobacter cerinus, Agrobacterium radiobacter* or *Pseudomonas alcaligenes.*

The fatty substance may be oleic acid, ricinic acid or any other naturally occurring or synthetic fatty acids mixed in diesel oil or weathered oil or any other hydrocarbon oil. Furthermore, the fatty substance can further comprise an oleophilic nutrient, such as nitrogen and phosphorus, preferably as available in oleophilic nutrient INIPOL®.

Generally, the oleophilic suspension comprises between 1% and 15% by volume of the fatty substance dissolved in hydrocarbon oil.

In a third aspect, the present invention relates to a method of making an oleophilic suspension comprising a fatty substance, hydrocarbon oil and a physiologically active bacterial culture of hydrocarbonoclastic bacteria for removing free floating oil from an aqueous environment by bio-dispersion followed by bio-utilization, the method comprising the steps of:

(i) enriching hydrocarbonoclastic bacteria from a sample of water;

(ii) admixing the enriched hydrocarbonoclastic bacteria with a fatty substance and hydrocarbon oil to form a suspension; and (iii) selecting those bacteria which are capable of bio-dispersion and bio-utilization.

DETAILED DESCRIPTION OF PREFERRED EMBODIMENTS

The following definitions apply:

By "bacterium having an ability to utilize hydrocarbons as the only source of carbon" is meant hydrocarbonoclastic bacteria.

By "fatty substance" is meant fatty acids and/or oils which are otherwise compatible with the bacteria, which are oleophilic and easily miscible with hydrocarbon oil and which are capable of forming a suspension of the bacteria. The substance may also be charged with inorganic or organic nitrogen, inorganic or organic phosphorus in a free state or as micro-emulsion.

By "free floating oil in an aqueous environment" is meant an oil, typically petroleum or a petroleum derivative, which floats on water, typically at a port or in a bay or in waste water of refinery or in tankers and ships as ballast or bilge water. The aqueous environment includes both fresh, salt and brackish water.

By "enriching hydrocarbonoclastic bacteria from a sample of water" is meant to isolate and cultivate consortium of hydrocarbon degrading bacteria from marine or fresh water sources through repeated subculture.

The following are the four stages of development of a method for removal of free floating oil from aqueous environment according to the present invention.

(1) A technique for isolation of an oleophilic suspension of marine bacterial cultures.

(2) A technique for assessing the activity of bacteria obtained as above.

(3) Application of marine bacterial culture for achieving dispersion and removal of free floating oil.

(4) Treatment of ballast/bilge water.

Technique for Isolation of Marine Bacterial Cultures.

In an earlier report on "Oil in the sea—inputs, fate and effects", it has been opined that biodegradation of hydrocarbons by natural populations of microorganisms represents one of the primary mechanisms by which petroleum and other hydrocarbons are eliminated from the environment. The objective of the present technique is to harness these hydrocarbonoclastic bacterial consortia and employ their hydrocarbon degrading abilities for removal of oil.

The protocol for isolation of a hydrocarbonoclastic population of indigenous bacteria was the conventional enrichment technique. Enrichment in the present case was carried out with low boiling point fractions of crude oil as represented by diesel oil or any other oil. Samples of seawater were collected from a local harbor or beach. In the present case, the water was collected from Prince Sound William at Alaska. This site was selected because of the fact that even ten years after the Exxon Valdez oil spill, the waters are still reported to be rich in population of oildegrading bacteria. It is possible to isolate a similar consortium of bacteria from different regions in the world. This will ensure employing indigenous bacteria for treatment in any respective coastal waters.

It has been reported that during the process of bioremediation of hydrocarbon oil, nitrogen and phosphorus are limiting factors forthe normal growth of bacteria. It is necessary to supplement these nutrients essential for the growth of microbes. The diesel oil was therefore, charged with 10% of an oleophilic fertilizer compound called INIPOL-EAP 22®. INIPOL® is marketed by M/S Elf Aquitaine, Paris, France. The compound contains 7.4% nitrogen and 0.7% elemental phosphorus. The seawater containing a heterotrophic population of bacteria was agitated on an orbital shaker at a speed of 280 rpm or as convenient. Since hydrocarbon is the sole source of available organic carbon, bacteria, which do not exhibit ability to utilize oil, do not survive. This enriches the population of hydrocarbonoclastic bacteria. This process is known as an enrichment process.

Obtaining a population of bacteria having an ability to utilize hydrocarbons as the only source of carbon may take as many as 16 weeks or even more. It is not possible to stipulate the exact period for obtaining a consortium of oil degrading bacteria but experience has shown that a minimum of 8 weeks would be required for isolation of a consortium of hydrocarbon degrading bacteria. The culture is desirably transferred repeatedly, even after the 8 weeks, to maintain the oil degrading property of the isolated consortium. This culture forms the basis of an Oleophilic Suspension of Physiologically Active Bacterial Culture (OSPABC). Cultures can also be maintained after 8 weeks initial isolation in hydrocarbon oils of different grades or properties to enrich this population with specialized oils. The oleophilic suspension of physiologically active bacterial culture obtained in this manner will show greater degree of degradation of a respective oil contaminants than the culture grown only on low fraction hydrocarbons like diesel.

A microbiological assay of the culture indicated the presence of bacteria and the distribution of species is likely to be site dependent. Species of bacteria identified in the present experiment are *Pseudomonas pseudoalkaligenes, Phenylobacterium immobile, Stenotrophomonas maltophilia, Gluconobacter cerinus, Agrobacterium radiobacter* and *Pseudomonas alcaligenes*. In most cases species belonging to Pseudomonas, Vibrio, Micrococcus, Acinetobacter etc. are likely to be more frequent in the culture. It may also be added that the dominance of species is site specific and species belonging to other genera and even yeast may be encountered. Any of these or other oil degrading bacteria may participate in biodispersion of polluting oil in marine or freshwater situations.

Technique for Assessment of Bacterial Activity.

Both microbiological and instrumental techniques have been employed to assess the oil degrading activities of the consortium of bacteria obtained through enrichment. Standard microbiological techniques were employed for recording the growth of bacterial consortium in the presence of test oil. Growth was recorded both by measuring optical density of the test medium and also by determining the total viable count employing membrane filtration technique. The Acridine Orange Direct Count (AODC) method was found unsuitable due to the interference of oil in the medium. Changes in the pH of medium were monitored but there was negligible variation in pH. It was not recorded routinely in the later studies.

Utilization of oil was ascertained by solvent extraction of the test oil from the medium. Loss of oil was determined gravimetrically and the residual oil was then made up to a known volume for further analysis. Loss of individual component was determined employing Gas Chromatographic techniques using Flame Ionization Detector (FID) employing prepacked column or capillary column DB 5 or any suitable column for such chromatographic analysis. Identification of individual constituents can be achieved by employing a gas chromatograph equipped with Mass Spectroscopy. The GC MS is an advanced research tool and may not be required for the present objective.

Laboratory studies have indicated that the consortium of bacteria obtained through the enrichment technique depends primarily on the hydrocarbon used as a source of organic carbon. In the absence of such a source the population has not been found to survive in seawater. This indicates that in the field, once the remediation of oil is achieved, the bacteria may die off naturally in the absence of any oil. The study has thus suggested that the treatment carried out in the field may not contribute to pollution due to bacteria in any way. It has been mentioned earlier that there is no appreciable change in the values of pH due to bacterial growth and metabolism. Thus bacterial activity may not contribute towards accelerated corrosion of metals and alloys particularly during bilge water treatment on board ships.

Method of Assessing the Biodispersive Activities.

Laboratory experiments have shown that the oleophilic suspension of physiologically active bacterial culture obtained through enrichment has an ability of utilizing the hydrocarbon oil during growth and metabolism. It was necessary to determine if the isolated consortium exhibited dispersion of oil through their activities. Experiments were therefore carried out in 25 liter narrow mouth glass jars either with a ground glass joint or rubber or polypropylene corks having four vents. These four vents will be required one each for inlet of air, one for exhaust, one for sampling and fourth one for introducing initial inoculum and if necessary for any incremental addition.

15.0 liters of seawater was filtered through commercially available Whatman No.1 filter paper. Experience has indicated that it may not be necessary to use sterile water. 15.0 ml. of test oil is added to the jar. The test oil may be diesel, weathered oil or crude oil or any type as per the requirement. The test oil is charged with INIPOL EAP-22® in the ratio of 10% of the volume before dispensing. Inoculum of bacterial culture grown for 24 hours is then added to the jar and made up to the volume of 15 liters. The volume of the culture may be 150 ml., 450 ml. or 750 ml. Optimum results were obtained with 750 ml of inoculum. This works out to be 5% of the total volume of seawater. Growth of bacteria was monitored regularly employing both the methods described earlier.

It has been observed that the optical density of the medium increased sharply on the third day and the value became stabilized on twentieth day. Values of total viable count of the bacteria however, did not match those of optical density. There was no sharp increase of the bacterial population. The increase in optical density may primarily be due to the fact that the test oil became dispersed within 72 hours and hence gave an increased value of turbidity. The loss of oil was also measured periodically and there was a loss of at least 44% of the original oil. The dispersion of oil recorded in these experiments has been attributed to the bacterial activity.

Studies also indicated that dispersion of oil is dependent upon the thickness of oil in the jar. Complete dispersion of oil less than or equal to 0.7 mm thick was achieved by bacterial activity within 4 days time whereas only 30% of oil of 3.3 mm thick were dispersed in the same period.

The experiments described above have shown that the marine bacterial consortium obtained through the above methods exhibited the ability of dispersing the test oil. This was further tested in the field and it was found that under dynamic conditions also there was dispersion of oil by the bacterial consortium. Dispersion of oil by the bacterial culture has been defined as "biodispersion". In view of the fact that dispersion of oil was the first step in utilization of oil, the present method has been identified as "biodispersion".

The effectiveness of the biodispersive activity along with bioutilization in removing floating oil spills was examined under different configurations. In each case dispersion of oil was recorded as the first stage for removal of oil. Time required for dispersion and bioremediation of polluting oil varied from system to system and on the volume of polluting oil. The method has thus been found to be applicable even in the field.

EXAMPLE 1

Bioremediation of Crude Oil Under Lab Conditions.

In recent years, it has been reported time and again that ships and tankers release bilge water and ballast water in the coastal waters and thereby pollute the environment. These are known as intentional discharges which account for 25% of total oil pollution. Although the polluting shipping agencies have been penalized wherever possible, it does not offer a solution to the problem. It has been observed that most ships, fishing boats and pleasure craft produce a large amount of bilge water. The amount of oil in this water may be 10 to 15% or sometimes even less. There is no provision of treating this water on board and transporting the water to coastal receiving facilities is cost prohibitive.

In order to examine the possibilities of employing the present method for bilge water treatment, the following experiment was designed in the laboratory. A commercially available rectangular glass tank of about 2'×1'×2' was filled with seawater from a local source. 30.0 ml of crude oil obtained for the purpose was overlaid on the water, which formed patches of oil over the surface of water. The oleophilic suspension of physiologically active bacterial culture was sprayed over the oil. In less than 24 hours the crude oil was distributed uniformly over the surface.

The oil was totally dispersed in water in less than 6 days time and the sample of oil analyzed after 12 days showed the presence of 146 mg/liter of total petroleum hydrocarbons. At the end of 30 days the analysis of water showed the value of TPH to be 8.6 mg/liter. The experiment represented a prototype of bilge water conditions. The removal of hydrocarbons by the bacterial culture thus shows immense possibilities of employing the technique for efficient treatment of bilge water in an environment friendly manner.

EXAMPLE 2
Field Trials in Miniature Oil Containing Booms.

The effectiveness of biodispersion accompanied by bioutilization of oil recorded in laboratory experiments was examined under field conditions. These experiments were conducted in miniature oil containing booms fabricated from inflatable tubes of an automobile tire. The tubes of tires were inflated to the maximum and the surface was protected with a rubber solution to prevent escape of air from the inflated tube. The inflated tubes were then lowered in the sea after applying additional weight of 15.0kg. The weight was so placed that it would keep the tube well balanced on water with ¾ of the surface below the water line.

Weathered oil collected from harbor was selected as the test pollutant. The oil was charged with 10% of INIPOL® and mixed well before employing it as the source of pollution. 100.0 ml. of this weathered oil was then dispensed in the well of the tube and the inflated tube was secured firmly. The well of the tube enclosed an area of 0.39 sq. Meter. The oil within this area forming an artificial oil spill was then sprayed with 100.0 ml. of a culture of consortium of bacteria grown for 24 hours in the laboratory. It was seen that the oil, which was unequally distributed within the well, was distributed uniformly in less than 24 hours. This indicates the process of biodispersion initiated by the oleophilic suspension of physiologically bacteria. At the end of 24 hours the color of oil was still dark. However, there appeared to be some loss signifying bioutilization. After 30 hours the color of oil became lighter and indicated some more loss. At the end of 48 hours however, there was no oil in the miniature oil boom and the water in the well became as clear as the one outside.

EXAMPLE 3
Field Trials in Modified Miniature Floating Booms.

Although the experiments in the inflated tubes showed good results, due to excessive heat in the environment, air in the tubes escaped and some of the experiments had to be abandoned. It was decided to examine the possibility of employing a new configuration, which will prevent such mishaps. In the new system, 200 liter drums were procured from a local supplier and both the top and the bottom of the drum were cut to obtain a polypropylene cylinder of about 0.78 meter square internal diameter. The wall of this cylinder was supported with four brackets of non-corrosive material to prevent the wall from collapsing due to hydrostatic pressure or wave action. Four polyurethane floats were fitted on each of the drums to achieve the required buoyancy for the structure. The modified miniature oil boom was placed in the harbor so that the lower end of the cylinder was at least 30 cm. below the water line. This would ensure that the oil spill created within this miniature boom did not escape. These modified miniature oil containing booms were lowered in the harbor and firmly secured.

Weathered oil from the harbor was once again selected as the source of artificial spill. As the internal area of the boom was increased, the volume of polluting oil was also increased to 250.0 ml. 250.0 ml of the oleophilic suspension of physiologically active culture of the consortium of bacteria grown in the laboratory for 24 hours was sprayed over the oil. There was similar transformation of the oil and the color of the oil was lighter as in earlier example. The oil was distributed uniformly in less than 10 hours time. The period for total loss of oil through biodispersion and bioutilization however, increased. It was observed that it required a period of 72 hours to 96 hours for complete bioremediation.

Both of the examples given here showed that the process of biodispersion described here is a precursor for an effective removal of floating oil spill.

EXAMPLE 4
Removal of Oil from an Oil Containing Boom.

Further experiments were carried for the removal of oil recorded in the field experiments employing a single 25 meter section of a riparian oil-containing boom obtained from agencies involved in combating oil pollution. The boom was inflated with the help of an air compressor and lowered into the harbor. The ends of the boom were joined with stainless steel connecting rods sealed with polyethylene sheets to prevent any accidental release of polluting oil. The inflated riparian boom gave an internal area of 360 square feet and the seawater contained in the boom was constantly flushed with tidal action. The boom was secured to a floating abandoned ship in an area in the harbor taking care not to disturb the normal movement of ships.

An artificial oil spill was created using weathered oil freshly collected from the harbor. 15.0 liters of this oil charged with INIPOL® were dispensed in the boom. The thickness of oil was calculated and it was found to be 0.22 mm. 1.0 liter of oleophilic suspension of physiologically active bacterial culture grown for 24 hours was sprayed with the help of an agricultural spraying device. In less than 5 hours the color of the weathered oil changed from black to a lighter shade. Uniform distribution of oil was indicative of bacterial action on the oil. After 5 days of treatment with the bacterial culture, the oil appeared to be distinctly lighter in color and also appeared to show a loss of 75% of the original volume. On ninth day, the film of oil became very thin and very light in color. The oil in the boom was completely remedied through bacterial action on tenth day and the water in the boom became as clear as the outside water. Repeated experiments showed the same results. The loss of oil in all the experiments was recorded on tenth day if the volume of polluting oil was kept constant.

All four of the above examples demonstrate that it was possible to remove floating oil from water employing an oleophilic suspension of physiologically active bacterial culture. The period of removal of oil however, varied with the volume of the polluting oil. The removal of oil recorded in these examples is attributed to the biological dispersion of oil followed by its utilization. The method has been defined as 'biodispersion' which is a new term. Its application for bilge water treatment can be considered a milestone in development since it is still constitutes the important source of oil pollution of coastal waters. The process described is thus effective against floating oil spills and also as pretreatment of bilge water or refinery waters containing oil.

Although only preferred embodiments of the invention have been specifically described above, it will be appreciated that many modifications and variations of the preferred embodiment are possible without departing from the spirit and intended scope of the invention.

What is claimed is:

1. A method for removal of free-floating oil from an aqueous environment by bio-dispersion and bio-utilization comprising the steps of:
   (i) isolating species/strains of bacteria having an ability to utilize hydrocarbons as the only source of carbon;
   (ii) admixing said bacteria with a fatty substance and hydrocarbon oil to form an oleophilic suspension comprising a physiologically active bacterial culture of hydrocarbonoclastic bacteria, said fatty substance comprising an oleophilic nutrient as a source of nitrogen and phosphorus for said bacteria, and
   (iii) applying said oleophilic suspension of said bacteria to a free floating oil in an aqueous environment to disperse and remove free-floating oil therefrom.

2. The method of claim 1, wherein said bacteria are obtained from the aqueous environment to be treated.

3. The method of claim 1, comprising isolating multiple species or strains of bacteria.

4. The method of claim 3, wherein said species or strains of bacteria are derived from Pseudomonas, Phenylobacterium, Stenotrophomonas, Gluconobacter, Agrobacterium, Vibrio, Acinetobacter, Micrococcus, or other oil degrading forms.

5. The method of claim 4, wherein said species or strain of bacteria is *Pseudomonas pseudoalkaligenes, Phenylobacterium immobile, Stenotrophomonas maltophilia, Gluconobacter cerinus, Agrobacterium radiobacter* or *Pseudomonas alcaligenes*.

6. The method of claim 1, wherein said bacteria is genetically manipulated.

7. The method of claim 1, wherein said fatty substance is an organic fatty acid.

8. The method of claim 7, wherein said organic fatty acid is a synthetic fatty acid.

9. The method of claim 7, wherein said organic fatty acid is a natural fatty acid.

10. The method of claim 7, wherein said organic fatty acid is oleic acid or ricinic acid.

11. The method of claim 1, wherein said fatty substance further comprises in an oleophilic nutrient.

12. The method of claim 11, wherein said oleophilic nutrient comprises nitrogen and phosphorus.

13. The method of claim 12 wherein said oleophilic nutrient is INIPOL®.

14. A method of making an oleophilic suspension comprising a fatty substance and a physiologically active bacterial culture of hydrocarbonoclastic bacteria for removing free floating oil from an aqueous environment by bio-dispersion followed by bio-utilization, said method comprising the steps of:

(i) enriching hydrocarbonclastic bacteria from a sample of water;

(ii) admixing said enriched hydrocarbonclastic bacteria with a fatty substance dissolved in hydrocarbon oil to form a suspension, said fatty substance comprising an oleophilic nutrient as a source of nitrogen and phosphorus for said bacteria;

(iii) selecting those bacteria which are capable of bio-dispersion and bio-utilization.

15. The process of claim 1, wherein said aqueous environment is an industrial wastewater containing oil.

16. The process of claim 15, wherein said aqueous environment is ballast water, bilge water or refinery wastewater.

17. The process of claim 1, wherein said aqueous environment is fresh water.

* * * * *